(12) United States Patent
Moser

(10) Patent No.: US 6,806,284 B1
(45) Date of Patent: Oct. 19, 2004

(54) PHOTOSENSITIZERS WITH LIGAND TARGETING PROPERTIES FOR TUMOR THERAPY

(75) Inventor: Jörg G. Moser, Düsseldorf (DE)

(73) Assignee: Ceram Optec Industries, Inc., East Longmeadow, MA (US)

( * ) Notice: Subject to any disclaimer, the term of this patent is extended or adjusted under 35 U.S.C. 154(b) by 0 days.

(21) Appl. No.: 09/599,660

(22) Filed: Jun. 22, 2000

(51) Int. Cl.$^7$ .................. C07D 487/22; A61K 31/40
(52) U.S. Cl. ...................... 514/410; 514/2; 514/19; 530/300; 540/145
(58) Field of Search ............... 514/410, 2, 19; 540/145; 530/300; 424/490

(56) References Cited

U.S. PATENT DOCUMENTS

| | | | |
|---|---|---|---|
| 5,502,037 | A | 3/1996 | Kondratyev |
| 6,169,078 | B1 | 1/2001 | Hughes et al. |
| 6,245,359 | B1 | 6/2001 | Milstein et al. |
| 6,287,857 | B1 | 9/2001 | O'Riordan et al. |
| 6,300,319 | B1 | 10/2001 | Manoharan |

OTHER PUBLICATIONS

Baily et al. 'DNA–Binding and DNA–Cleaving Properties of Synthetic Model Agaglu Related to the Antitumor Drugs AMSA and Bleomycin.' vol. 152, No. 2, pp. 695–702. 1988.*

Dougherty TJ. "Photosensitizers: Therapy and detection of malignan–tumors" Photochem. Photobiol. 45(6): 879–889, (1987).

Dougherty TJ. "Photodynamic therapy" Photochem. Photobiol. 58(6): 895–900, (1993).

(List continued on next page.)

Primary Examiner—Brenda Brumback
Assistant Examiner—Anish Gupta
(74) Attorney, Agent, or Firm—BJ Associates; Bolesh J. Skutnik

(57) ABSTRACT

The present invention provides a drug delivery system wherein a "parachute" structure is coupled to a therapeutic compound. The "parachute" structure comprises hydrophilic branched molecules with a defined action diameter. The complex (a parachute structure coupled with a therapeutic compound) is either fixed at a cell membrane or delivered to a defined distance from the membrane within the cell. The membrane-anchoring/localizing effect of the parachute is achieved by hydrophilic structures linked with a branching unit of desired therapeutic compounds. Furthermore, the parachute structures can be connected by a spacer (e.g. β-amino acids, γ-amino butyric acid, or poly-amino acids) instead of directly binding to the therapeutic compound, so that the therapeutic compounds can be localized within the cells at a defined distance from the cell membrane. A spacer containing a breaking point can determine the time span, during which the drug exhibits its therapeutic activity. The hydrophilic residues can also carry signals for targeting the parachute-therapeutic complex to a defined tissue type. This can be mediated by an antibody which is specific for a tumor marker. Alternatively, a Biotin can be attached at C6 position of the sugar and then react with an Avidin-labeled tumor-specific antibody. The parachute function may also be achieved by other, more bulky hydrophilic structures such as oligosaccharides connected to the branching unit. Such sugar oligomers have specific attachment points to cell selectins, and therefore do not need additional molecular structures to target a specific tumor tissue. The use of the parachute structure gives the advantages of being able to localize a photosensitizer or chemotherapeutic drug at the site within a cell where it can destroy the tumor cell most effectively. This reduces the level of necessary systemic doses of the drugs, promotes drug excretion, and therefore considerably reduces side effects of the therapy.

11 Claims, 3 Drawing Sheets

OTHER PUBLICATIONS

Sokolov V. "Multicourse PDT of malignant tumors: the influence of the primary tumor, metastatic spreading and homoestasis in cancer patients" SPIE Biomedical Optics 3191, 322–329 (1996).

Moser JG "Definitions and general properties of 2nd and 3rd generation photosensitizers" and "Carrier and delivery systems" "Photodynamic tumor therapy—2nd and 3rd generation photosensitizers" pp. 3–8 127–136, Moser JG ed, Harwood Academic Publishers, London, 1998.

Hirth A et al., "New biotinylated phthalocyanines for the photodynamic therapy of cancer" SPIE Biomed. Optics 3191, 309–314, (1997).

Matz et al., "Fluorescent proteins from nonbioluminescent anthozoa species" Nat. Biotechnol. 17(10): 969–73, (1999).

Kessel D et al., "Use of fluorescent probes for characterizing sites of photodamage" The Spectrum 6(2): 1–6, (1993).

* cited by examiner

PHOTOSENSITIZERS WITH LIGAND TARGETING PROPERTIES FOR TUMOR THERAPY

BACKGROUND OF THE INVENTION

1. Field of the Invention

The present invention relates to photodynamic therapy and chemotherapy, wherein a "parachute" structure is used to deliver a therapeutic agent to a defined subcellular location, and therefore the action of the therapeutic agent, such as destroying tumor cells, is achieved more effectively.

2. Invention Disclosure Statement

During the last two decades, there has been an increasing interest in utilizing photosensitizers for cancer therapy, where the technique is known as Photodynamic Therapy (PDT). Dougherty T J, *Photosensitizers: Therapy and detection malignant tumors,* Photochem. Photobiol, 45(6): 879–889, (1987) and Dougherty T J, *Photodynamic therapy,* Photochem. Photobiol, 58(6): 895–900, (1993) describe a technique where singlet oxygen, oxygen radicals, and superoxides/peroxides are produced by in situ photosensitization of previously applied chromophores, and thus destroy the malignant cells. The technique utilizes non-toxic, photosensitizing drugs in combination with non-hazardous irradiation, and has the potential of being more selective yet no less effective when compared with the commonly used chemotherapy or radiotherapy. It is therefore expected to increase the quality of life for treated patients Moreover, Sokolov V. et al., *Multicourse PDT of malignant tumors: the influence of the primary tumor, metastatic spreading and homoestasis in cancer patients.* SPIF Biomedical Optics 3191, 322–329 (1996) shows that no scars are observed after removal of the tumors using this technique and the surrounding muscular structures are fully functional.

The photosensitizers used in PDT need to have a high quantum yield for singlet oxygen production, as well as characteristics of high affinity and selectivity for the malignant tissue. Porphyrins have a high quantum yield for the formation of an excited triplet state. The difference between the energies of triplet state and ground-state oxygen makes them good energy donors to transfer its energy to the ground state to form singlet oxygen. One experimental drug known as Photofrin II (a purified version of hematoporphyrin derivative) is currently involved in randomized clinical trials. Other photosensitizing drugs used in photodynamic therapy procedures include phthalocyanines, merocyanine 540, substituted purines, xanthenes (Rhodamine 123), cationic cyanine dyes, chlorines, chalcogenapyrylium dyes containing selenium or tellurium atoms in the chromophore, phenothiazinium derivatives, benzophenoxoniums (Nile Blue A) and triarylmethanes (Methylene Blue, Victoria Blue BO [VB-BO]).

Illumination of the target site by an appropriate light source, such as a sunlamp, an argon-pumped dye laser, or more recently, diode lasers, induces the cytotoxic effect on the cells of the target site by one of two proposed mechanisms. In Type I photosensitization, the electronically excited drug reacts directly with a biological substrate, forming radicals which can initiate subsequent radical reactions that induce cytotoxic damage. Type II photosensitization involves energy transfer from the electronically excited drugs to oxygen, producing singlet oxygen which subsequently produces cytotoxic oxygenated products destroying the cell membrane of tumor (and vascular endothelial) cells directly.

Although remarkable results have been obtained in some PDT trials, several problems remain. The low solubility of some of the sensitizers reduces their usefulness for intravascular administration because it can provoke thromboembolic events. The use of liposomes as transport vehicles can overcome the problem of the solubility, but there still remains the difficulty of directing the sensitizers to specific target sites. Moreover, liposomes administered intravenously to subjects are rapidly accumulated in the reticuloendothelial system often inducing several severe allergic reactions. High liposome concentration is thereby rapidly achieved in organs with fenestrated capillaries, such as the liver, spleen, and bone marrow. Liposomal systems can be effective in treating tumors that infiltrate these organs (such as hematologic malignancies), but have been less useful in treating targeted tumors in other anatomical locations.

Very high systemic doses of the sensitizer must often be given to achieve therapeutic levels at irradiated tumor sites, hence many sites in the body are nonselectively infiltrated by the sensitizer. As the amount of the applied photosensitizer increases, the chances of its accumulation in normal tissues and the accompanying risk of damaging non-malignant sites profoundly increases.

There have been many attempts to increase the specificity of the photosensitizers for the tumor and thereby concentrating a sufficient amount of molecules in the tumor cells. Moser J G *"Definition and general properties of $2^{nd}$ and $3^{rd}$ generation photosensitizers" and "carrier and delivery systems" in Photodynamic tumor therapy $2^{nd}$ and $3^{rd}$ generation photosensitizers,* pp. 3–8 and 127–136 respectively, [Moser, J G ed, Harwood Academic Publishers, London, (1998)] describe an approach of the coupling of several molecules of the dye with tumor specific antibodies which resulted in excellent phototoxicity in vitro. However, in vivo this method failed due to the recognition of the vast complex by the reticuloendothelial system, subsequent accumulation in the liver, and digestion of the compound before it reached the target site. Hirth A et al., *New biotinylated phthalocyanines for the photodynamic therapy of cancer.* SPIE Biomed. Optics 3191, 309–314, (1997) disclosed a more promising approach using polyphasic tumor targeting. Here, the antibodies are coupled with only minimum deviation substituents like biotin, so that they are not recognized by the reticuloendothelial system. After clearing the excessive biotinylated antibodies in the system, the photosensitizer coupled to avidin can be administered and accumulate at the cells labeled by the antibody. This method still has to be developed further for in vivo use in tumor therapy. But even if the targeting of the dye to the tumor would be successful, still an amount of at least $10^7$ photosensitizer molecules per cell has to be reached for the effective destruction of the tumor, which none of the described techniques have successfully achieved.

The reduction of the amount of photosensitizer molecules necessary for successful therapy could be achieved by more selective targeting of the dyes to the sites in the cell, where the compounds can develop the most effective action for the destruction of the malignant cells. Specific subcellular targeting of photosensitizers was only rarely performed and observed. One example is Rhodamine 123 targeting mitochondrial membranes. Matz et al, *Fluorescent proteins from nonbioluminescent Anthozoa species,* Nat. Biotechnol, 17(10): 969–73, (1999) describes red-fluorescent targeting proteins for achieving the same effect. Kessel D, *Use of fluorescent probes for characterizing sites of photodamage,* The Spectrum 6(2), 1–6, (1993) describes other examples and techniques of detection. The frequent localization of bacteriochlorophyll derivatives is at the Golgi apparatus. However, both localizations are not very deleterious for cancer cells since these cells obtain their energy from basal cytoplasmic metabolism.

In summary, there are various attempts to increase the specificity of phototherapeutic drugs and thereby to reduce the doses necessary for the successful photodynamic therapy of tumors. However, no satisfying solution to this problem has been presented so far. The present invention provides a novel method to enhance the effect of photosensitizers or other therapeutic compounds on cells to achieve successful therapy with reduced doses of the drugs.

BRIEF SUMMARY AND OBJECTIVES OF THE INVENTION

It is an object of the present invention to provide a system for and method of localizing therapeutic compounds at the most sensitive sites in a cell, thereby reducing therapeutic doses of the drug and in turn reducing the side effects of the therapy.

It is another object of the present invention to localize therapeutic compounds at cell membranes which results in a reduction of the dosage needed by a factor of 10–100 or more while achieving the same therapeutic effect.

It is a further object of the present invention to localize therapeutic compounds not only at a cell membrane, but also at defined distances to the membrane within the cells to optimize the destroying properties of the respective drug.

Still another object of the present invention is to modify the hydrophilic residues of the delivery structure so that it can also carry signals for targeting of the therapeutic complex to a specific tissue type.

Briefly stated, the present invention provides a drug delivery system wherein a "parachute" structure is coupled to a therapeutic compound. The "parachute" structure comprises hydrophilic branched molecules with a defined action diameter, where action diameter is the distance between the hydrophilic moieties that is necessary to localize the complex in the cell membrane. The complex (a parachute structure coupled with a therapeutic compound) is either fixed at a cell membrane or delivered to a defined distance from the membrane within the cell. The membrane-anchoring/localizing effect of the parachute is achieved by hydrophilic structures linked with a branching unit of desired therapeutic compounds (such as photosensitizers and chemotherapeutics). For example, di-glucosamine, a hydrophilic structure of a defined action diameter, functions to retard the molecules at the cell membrane, and thus avoids or slows deeper penetration of the therapeutic compounds into the cell during the short time span before irradiation. The defined action diameter can be achieved by using a branching unit, which can be triazine trichloride or trimesinic acid trichloride, to connect the therapeutic compound such as porphyrin over a diamide spacer bridge with two glucosamine residues. Furthermore, the parachute structures can be connected by a spacer (e.g. β-amino acids, γ-amino butyric acid, poly-amino acids, aliphatic, aromatic or heterocyclic molecules) instead of directly binding to the therapeutic compound, so that the therapeutic compounds can be localized within the cells at a defined distance from the cell membrane. A spacer containing a breaking point (for example, it can be cleaved by the action of cellular enzymes) can determine the time span, during which the drug exhibits its therapeutic activity. The hydrophilic residues can also carry signals for targeting the parachute-therapeutic complex to a defined tissue type. This can be mediated by an antibody which is specific for a tumor marker. Alternatively, a Biotin can be attached at C6 position of the sugar and then react with an Avidin-labeled tumor-specific antibody. The Biotin-Avidin system has the advantage of minimizing the size of the delivery structure so that it will not be recognized by the reticuloendothelial system and get destroyed. The parachute function may also be achieved by other, more bulky hydrophilic structures such as oligosaccharides connected to the branching unit. Such sugar oligomers have specific attachment points to cell selecting, and therefore do not need additional molecular structures to target a specific tumor tissue. The use of the parachute structure gives the advantages of being able to localize a photosensitizer or chemotherapeutic drug at the site within a cell where it can destroy the tumor cell most effectively. This reduces the level of necessary systemic doses of the drugs, promotes drug excretion, and therefore considerably reduces side effects of the therapy.

The above, and other objects, features and advantages of the present invention will become apparent from the following description read in conjunction with the accompanying drawings.

DETAILED DESCRIPTION OF PREFERRED EMBODIMENTS

The plasma membrane of the cell is a selective barrier for the influx of external substances in the cell. Moreover, the cell membranes have a very high condensor potential, expressed as a field strength=$10^5$ V/cm. Consequently, disturbances at the cell membrane are highly efficient for the destruction of the whole cell. The present invention achieves exclusive localization of a therapeutic compound at a cell membrane or at a defined distance from the membrane within the cell by linking the drug to a parachute structure. Hydrophilic branched molecules such as di-glucosamine function as a parachute because of their hydrophilic nature and the distance between the molecules (action diameter). Such characteristics of the hydrophilic branched molecules will keep them from entering a cell while a drug attached to them penetrates the cell. Since the parachute is built up in a way that the distance between the hydrophilic branched molecules and the drug can vary as desired by adding different spacer molecules, the drug is delivered to a cell either very near to the cell membrane (when there is no spacer molecules attached) or at a defined distance from the cell membrane within the cell depending on the type and number of spacer molecules used. Spacer molecules can be β-aminoacids, γ-amino butyric acid, poly-amino acids such as poly-lysine, poly-serine, poly-threonine, or aliphatic, aromatic or heterocyclic molecules. Different targeting signals (such as antibodies or Biotins) can be attached to the hydrophilic branched molecules thus directing the entire complex to a specific tissue type such as a tumor or cancer. The hydrophilic branched molecules can also be sugar oligomers with specific attachment points at cell selectins for targeting purposes.

The parachute structure is particularly useful when the therapeutic compound is a photosensitizer, such as a porphyrin, which is commonly used in photodynamic therapy. The parachute structure will hold photosensitizers near the cell membrane during radiation activation so that the drug is much more effective. The dosage of photosensitizer needed when using the parachute structure is reduced by a factor of about 100 or more to achieve the same effect as when the drug is used in the conventional way. Porphyrin molecules containing only one propionic acid residue can be attached to the hydrophilic branched molecules through a branching unit, such as triazine trichloride or trimesinic acid trichloride. Moreover, the present invention has advantages when the therapeutic compound attached to the parachute is a chemotherapeutic drug like Merphalane, which needs membrane contact for specific functioning and has serious side effects on the liver function.

Figure 1:
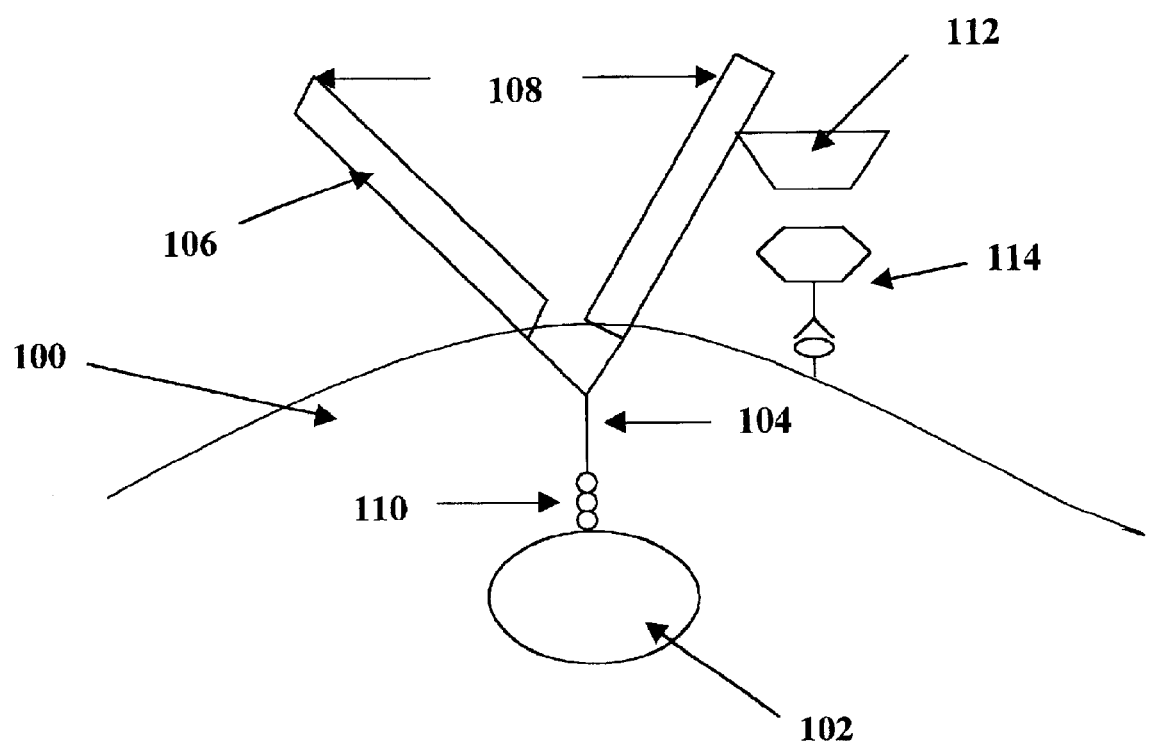
FIG. 1 shows a general embodiment of a drug delivery system.

FIG. 1 demonstrates a general scheme of a drug delivery system. According to the present invention, the system is constructed by attaching therapeutic compound 102 to a parachute structure. The parachute structure comprises hydrophilic branched molecules 106 with defined action diameter 108. The parachute structure can be directly linked to therapeutic compound 102, or it can be linked by branching unit 104, or branching unit 104 plus spacer 110 to therapeutic compound 102. The parachute structure can also be modified to target specific cell type such as cancer cell 100. For example, Biotin 112 can be attached to the parachute structure and reacts to Avidin-labeled tumor-specific antibody 114.

Figure 2:
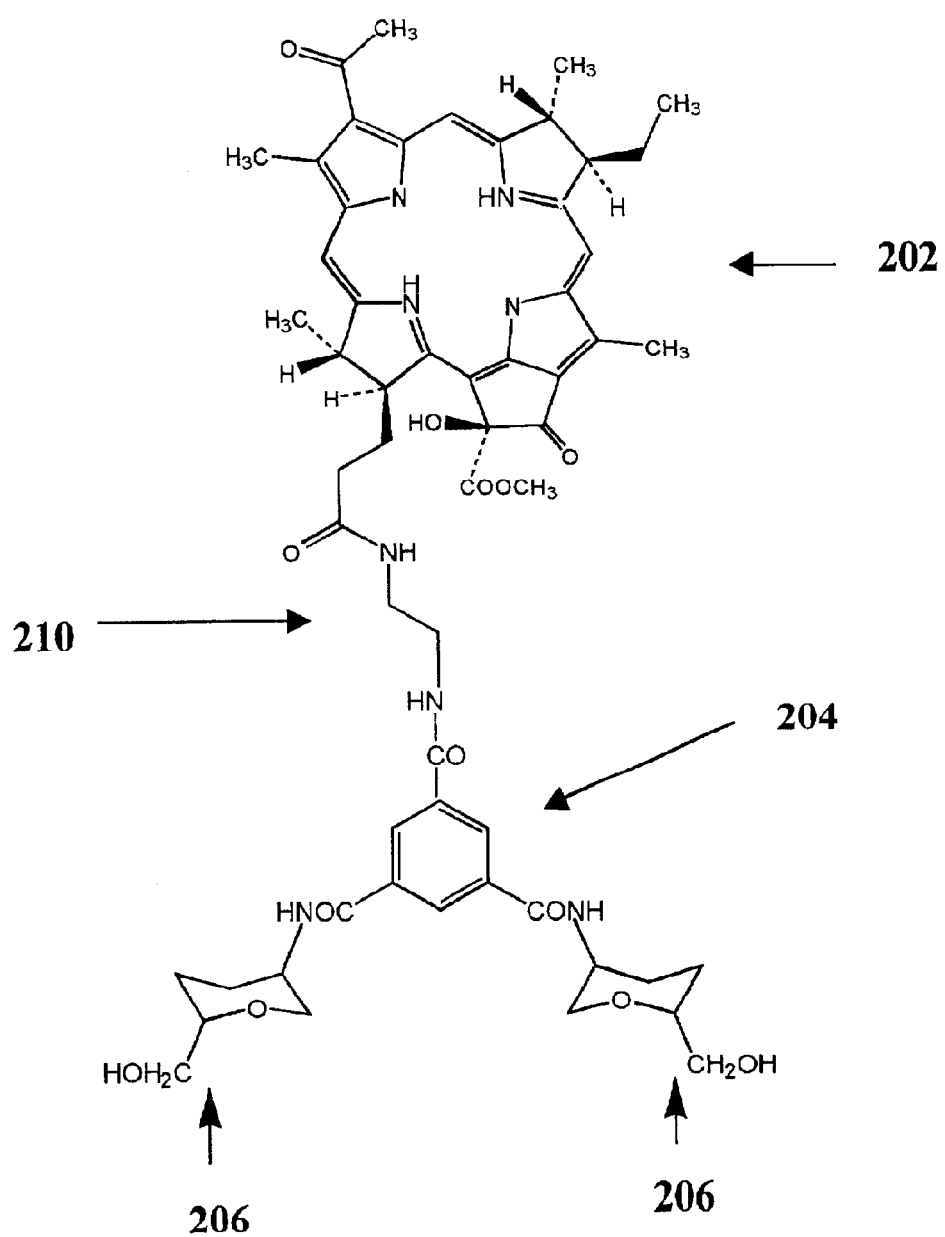
FIG. 2 illustrates an example of a photosensitizer coupled by a spacer to a parachute structure consisting of a branching unit carrying two glucosamine residues.

FIG. 2 shows the hydrophilic moiety of parachute structure consists of two glucosamine residues 206. The parachute effect is achieved by the linkage of aminosugars to branching unit 204, triazine trichloride or trimesinic acid trichloride. Spacers 210 can be linked to branching unit 204. Spacer 210 can be β-aminoacids, γ-amino butyric acid, or poly-amino acids. Also spacers with preformed breaking points, e.g. amino acid sequences recognized by cellular proteases, could be used. As an example of therapeutic agents, OH-bacteriopheophorbide 202 is used, which is connected at the propionic acid side chain at C17 with an ethyldiamine group and further with the parachute structure. The free amino group of the resulting amide reacts readily with branching unit 204. The glucosamine residues can be modified to mediate the tumor specific targeting of the delivery system.

Figure 3:
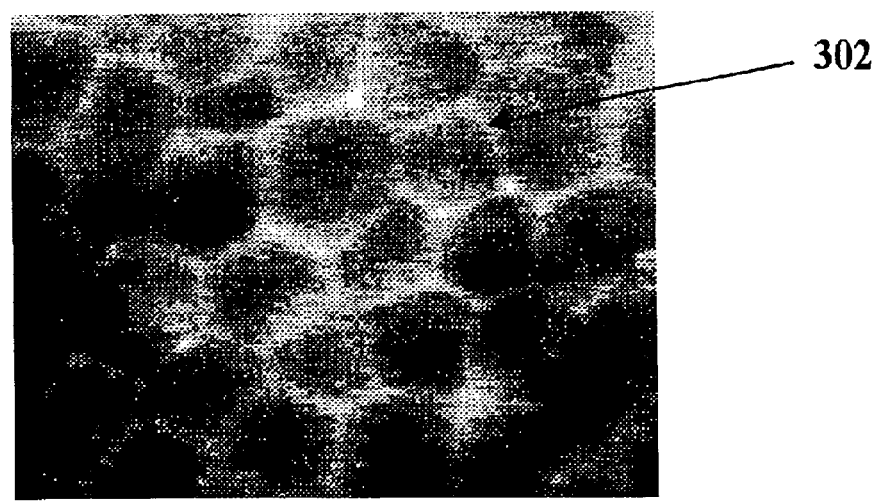
FIG. 3 demonstrates exclusive location of a modified photosensitizer at the cell membrane (fluorescence).

FIG. 3 illustrates the detection of the complex at the cell surface by fluorescence microscopy. Fluorescence is induced on the cells with green light (546 nm), and the localization of complex 302 is observed at the cell membrane.

The present invention is further illustrated by the following examples, but is not limited thereby.

EXAMPLE 1

Construction of a Parachute with Therapeutic Compound a. Bacteriopheophorbide (therapeutic compound) is activated in DMF by incubation with 1.1 MolEq diisopropyl carbodiimide at 0° C. for 30–60 min. This mix is added dropwise to a solution of 5 MolEq diaminoethane in DMF, dissolved under addition of 1.1 MolEq dimethyl aminopyridine. The product is isolated by ion exchange chromatography on CM-Cellulose or SP-Sepharose in DMF using a formiate gradient.

b. Addition of the spacer. A solution of triazine trichloride in toluene is centrifuged to remove unsoluble matter and titrated at room temperature with 2 MolEq of β-alanine or γ-amino butyric acid in the presence of $K_2CO_3$. The reaction proceeds overnight. The white precipitate is dissolved in methanol and reacted with the product of (1) at 85° C.

c. Synthesis of the branched glucosamine moiety. The product (2) is purified by ion exchange chromatography on DEAE-Sephadex or QAE-Sepharose in methanol-formiate gradients and freeze-dried. After activation by diisopropyl carbodiimid in DMF, a watery solution of glucosamine is added. Alternatively, a solution of methylglucosamine in 2-methoxy ethanol is added without activation.

EXAMPLE 2

Treatment of Patients with the Substance and PDT

For a patient, a dose of 0.8–1.0 mg/kg of the product should be sufficient for intravenous injection. Irradiation should follow at 760 nm and after only 15 min. The light power should be reduced to 200 mW, and no more than 20 $J/cm^2$ should be applied. The persistence of the dye in blood can be followed by fluorescence spectrometry and a reduction by a factor of 10 should be observed after 1 week.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A complex for delivery and application of drugs to cells at their membranes comprising:

a parachute structure, having a preselected action diameter;

a therapeutic compound, being a photosensitizer;

wherein said parachute structure is two hydrophilic moieties attached to a branching unit, defining said preselected action diameter;

wherein said branching unit connects said hydrophilic moieties and said therapeutic compound and is selected from the group consisting of triazine trichloride and trimesinic acid trichloride;

wherein said photosensitizer is chosen from the group consisting of bacteriopheophorbide and pheophorbide; and wherein said two hydrophilic moieties are glucosamines.

2. The complex according to claim 1, wherein said branching unit within said parachute structure is bonded to a spacer, wherein said spacer is a molecule selected from the group consisting of beta-amino acids and gamma-amino butyric acid and is also bonded to said therapeutic compound, thus completing the connection between said branching unit and said therapeutic compound.

3. The complex according to claim 1, wherein said branching unit within said parachute structure is bonded to a spacer, wherein said spacer is a molecule selected from the group consisting of poly-amino acids and an amino acid sequence and is also bonded to said therapeutic compound, thus completing said connection between said branching unit and said therapeutic compound.

4. The complex according to claim 3, wherein said amino acid sequence has an enzyme cleavable breaking point.

5. The complex according to claim 1, wherein said parachute structure is modified by a bonding of a Biotin at a C6 position of said glucosamine and then said Biotin is reacted with an Avidin-labeled tumor-specific antibody.

6. The complex according to claim 1, wherein said complex can be used to photochemically destroy cells, and wherein said cells are prokaryotic.

7. The complex according to claim 1, wherein said complex can be used to photochemically destroy cells, and wherein said cells are eukaryotic.

8. The complex according to claim 6, wherein said prokaryotic cells are bacteria.

9. The complex according to claim 7, wherein said eukaryotic cells are human/animal cells.

10. A method for the selective destruction of eukaryotic or prokaryotic cells comprising the steps of:
   a. administering the complex of claim 1 to a preselected tumor region within a patient;
   b. waiting for a pretreatment time interval sufficient to allow said complex to localize at cell membranes within said tumor region; and
   c. irradiating said tumor region for a defined treatment time interval and intensity to activate said photosensitizer; wherein said treatment time interval and intensity are sufficient to achieve destruction of cells within said tumor region.

11. A method for the selective destruction of eukaryotic or prokaryotic cells comprising the steps of:
   a. administering the complex of claim 2 to a preselected tumor region within a patient;
   b. waiting for a pretreatment time interval sufficient to allow said complex to localize at cell membranes within said tumor region; and
   c. irradiating said tumor region for a defined treatment time interval and intensity to activate said photosensitizer; wherein said treatment time interval and intensity are sufficient to achieve destruction of cells within said tumor region.

* * * * *